United States Patent [19]

Kirchner et al.

[11] Patent Number: 5,364,834
[45] Date of Patent: Nov. 15, 1994

[54] USE OF OXIME ETHER DERIVATIVES FOR BIOREGULATION IN PLANTS

[75] Inventors: Juergen Kirchner, Viernheim; Oskar Schmidt, Heidelberg; Klaus Grossmann; Wilhelm Rademacher, both of Limburgerhof; Michael Hepp, Ladenburg; Thomas Zierke, Boehl-Iggelheim, all of Germany

[73] Assignee: BASF Aktiengesellschaft, Ludwigshafen, Germany

[21] Appl. No.: 840,202

[22] Filed: Feb. 24, 1992

[30] Foreign Application Priority Data

Mar. 1, 1991 [DE] Germany .................. 4106509

[51] Int. Cl.$^5$ ............... A01N 37/52; A01N 37/44
[52] U.S. Cl. ................................. 504/319; 504/320
[58] Field of Search .............. 71/65, 68, 111, 113; 504/319, 320

[56] References Cited

U.S. PATENT DOCUMENTS

| | | | |
|---|---|---|---|
| 4,324,579 | 4/1982 | Farge et al. | 71/74 |
| 4,581,060 | 4/1986 | Martin | 71/94 |
| 4,584,014 | 4/1986 | Patterson | 71/113 |
| 4,744,811 | 5/1988 | Schulz et al. | 71/68 |

FOREIGN PATENT DOCUMENTS

| | | |
|---|---|---|
| 182407 | 5/1986 | European Pat. Off. . |
| 46-007928 | 2/1971 | Japan . |
| 46-007932 | 2/1971 | Japan . |

OTHER PUBLICATIONS

Abeles, F. B., *Ethylene in Plant Biology*, N.Y. Academic Press, 1973 pp. 103 and 111.
Chem. Abst. 54, 5524d, citing Vecchio et al Atti. Soc. peloritana Sci. Fig. Matie Nat., 4, 147-161 (1957).
Chem. Abst. 96 142207, (1982) citing Zorina et al, Zh. Obshch. Khim., 52 223-224 (1982).
Biochemistry and Physiology of Plant Hormones, 2nd Ed., Springer Verlag, N.Y. 228-2541 (1989).
Sisler et al, Bio Science, 34 (4), 234-238 (1984).
Yang et al, Ann. Rev. Plant, Physiol. 35 155-189 (1984).
Gardner et al, Plant Physiol., 90, 291-295 (1989).
Katekar et al, Plant Physiol. 66, 1190-1195 (1980).

Primary Examiner—Richard L. Raymond
Assistant Examiner—B. Bembenick
Attorney, Agent, or Firm—Keil & Weinkauf

[57] ABSTRACT

Oxime ether derivatives of the general formula I $$R^1R^2C=NO-CH_2-COOR^3 \qquad I$$

where $R^1$ and $R^2$ independently of one another are each hydrogen or $C_1-C_6$-alkyl or, together with the carbon atom to which they are bonded, are $C_5$- or $C_6$-cycloalkyl and $R^3$ is hydrogen or $C_1-C_6$-alkyl, are used for bioregulation in plants.

4 Claims, No Drawings

USE OF OXIME ETHER DERIVATIVES FOR BIOREGULATION IN PLANTS

The present invention relates to the use of oxime ether derivatives of the general formula I $$R^1R^2C=NO-CH_2-COOR^3 \qquad I$$

where $R^1$ and $R^2$ independently of one another are each hydrogen or $C_1$-$C_6$-alkyl or, together with the carbon atom to which they are bonded, are $C_5$- or $C_6$-cycloalkyl and $R^3$ is hydrogen or $C_1$-$C_6$-alkyl, for bioregulation in plants.

The present invention furthermore relates to methods for bioregulation in plants.

The literature discloses oxime ether derivatives of the formula I as intermediates for the preparation of bioregulators (EP-A 243 834). However, these intermediates were not found to have biological activity. This literature also discloses that alkoxycarbonylmethyl esters of the compounds I have bioregulatory activities.

It is an object of the present invention to provide novel effective bioregulators.

We have found that this object is achieved and that the oxime ether derivatives I defined at the outset are suitable for bioregulation in plants.

The oxime ether derivatives I can be prepared by various methods.

The compounds are obtained, for example, in a conventional manner by condensing a carbonyl compound of the general formula II with hydroxylamine-O-acetic acid or an ester III thereof according to the equation below.

$$R^1R^2C=O + H_2NO-CH_2-COOR^3 \longrightarrow$$

$$\text{II} \qquad \text{III}$$

$$R^1R^2C=NO-CH_2-COOR^3$$

$$\text{I}$$

(Vecchio et al., Atti. soc. peloritana Sci. fis. Mat. e Nat., 4, (1957-58) 163–82, corresponding to C.A. 54, 5524 d).

In another process, an oxime of the general formula IV is reacted, likewise in a known manner, with an alpha-haloacetic acid derivative of the general formula V according to the equation below.

$$R^1R^2C=NOH + Hal-CH_2-COOR^3 \longrightarrow$$

$$\text{IV} \qquad \text{V}$$

$$R^1R^2C=NO-CH_2-COOR^3$$

$$\text{I}$$

In formula V, Hal is halogen, in particular chlorine or bromine (Zorina et al., Zh. Obshch. Khim. 52 (1982), 223–224, corresponding to C.A. 96, 142 207d).

In view of the intended use of the compounds I for bioregulation in plants, suitable substituents are the following:

$R^1$ and $R^2$ independently of one another are each hydrogen or $C_1$-$C_6$-alkyl, such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl, or $R^1$ and $R^2$ together with the carbon atom to which they are bonded, are $C_5$- or $C_6$-cycloalkyl, such as cyclopentyl or cyclohexyl.

With regard to their use for bioregulation in plants, particularly preferred oxime ether derivatives of the formula I are those in which $R^1$ is hydrogen or methyl or $R^1$ and $R^2$, together with the carbon atom to which they are bonded, are cyclohexyl.

Other preferred compounds I are those in which $R^3$ is hydrogen.

Examples of particularly preferred oxime ether derivatives of the general formula I are shown in the Table below.

TABLE $R^1R^2C=NO-CH_2-COOR^3 \quad I$

| No. | $R^1$ | $R^2$ | $R^3$ |
|---|---|---|---|
| 1 | H | $CH_3$ | H |
| 2 | H | $CH_3$ | $CH_3$ |
| 3 | H | $CH_3$ | $CH_2CH_3$ |
| 4 | H | $CH_3$ | $CH_2CH_2CH_3$ |
| 5 | H | $CH_3$ | $CH(CH_3)_2$ |
| 6 | H | $CH_3$ | $C(CH_3)_3$ |
| 7 | H | $CH_3$ | $(CH_2)_5CH_3$ |
| 8 | H | $CH_2CH_3$ | H |
| 9 | H | $CH_2CH_3$ | $CH_3$ |
| 10 | H | $CH_2CH_3$ | $CH_2CH_3$ |
| 11 | H | $CH_2CH_3$ | $CH_2CH_2CH_3$ |
| 12 | H | $CH_2CH_3$ | $CH(CH_3)_2$ |
| 13 | H | $CH_2CH_3$ | $C(CH_3)_3$ |
| 14 | H | $CH_2CH_3$ | $(CH_2)_5CH_3$ |
| 15 | $CH_3$ | $CH_3$ | H |
| 16 | $CH_3$ | $CH_3$ | $CH_3$ |
| 17 | $CH_3$ | $CH_3$ | $CH_2CH_3$ |
| 18 | $CH_3$ | $CH_3$ | $CH_2CH_2CH_3$ |
| 19 | $CH_3$ | $CH_3$ | $CH(CH_3)_2$ |
| 20 | $CH_3$ | $CH_3$ | $C(CH_3)_3$ |
| 21 | $CH_3$ | $CH_3$ | $(CH_2)_5CH_3$ |
| 22 | $CH_3$ | $CH_2CH_3$ | H |
| 23 | $CH_3$ | $CH_2CH_3$ | $CH_3$ |
| 24 | $CH_3$ | $CH_2CH_3$ | $CH_2CH_3$ |
| 25 | $CH_3$ | $CH_2CH_3$ | $CH_2CH_2CH_3$ |
| 26 | $CH_3$ | $CH_2CH_3$ | $CH(CH_3)_2$ |
| 27 | $CH_3$ | $CH_2CH_3$ | $C(CH_3)_3$ |
| 28 | $CH_3$ | $CH_2CH_3$ | $(CH_2)_5CH_3$ |
| 29 | —$CH_2CH_2CH_2CH_2CH_2$— | | H |
| 30 | —$CH_2CH_2CH_2CH_2CH_2$— | | $CH_3$ |
| 31 | —$CH_2CH_2CH_2CH_2CH_2$— | | $CH_2CH_3$ |
| 32 | —$CH_2CH_2CH_2CH_2CH_2$— | | $CH_2CH_2CH_3$ |
| 33 | —$CH_2CH_2CH_2CH_2CH_2$— | | $CH(CH_3)_2$ |
| 34 | —$CH_2CH_2CH_2CH_2CH_2$— | | $C(CH_3)_3$ |
| 35 | —$CH_2CH_2CH_2CH_2CH_2$— | | $(CH_2)_5CH_3$ |

The compounds of the formula I can influence virtually all stages of development of a plant in different ways and are therefore used as bioregulators.

The active ingredients to be used according to the invention can be fed to the crops both via the seed (as seed dressings) and via the soil, ie. through the root and, particularly preferably, via the foliage by spraying. In the case of parts of plants, the active ingredient can be fed by both immersion and spraying as well as via the water supplied, for example in the case of cut flowers.

Because of the good toleration by plants, the application rate can be greatly varied.

In seed treatment, in general from 0.001 to 50 g, preferably from 0.01 to 10 g, of active ingredient are required per kilogram of seed. For foliage and soil treatment, in general doses of from 0.001 to 10, preferably from 0.01 to 1, kg/ha are to be regarded as sufficient. For the treatment of parts of plants, in general from 0.001 mg to 50 g, preferably from 0.01 mg to 1 g, of active ingredient are required per kilogram of plant parts. For keeping cut flowers fresh, the active ingredient concentrations in the water supplied are in general from 0.001 to 10, preferably from 0.05 to 1, g/l.

The formulations or the ready-to-use preparations produced therefrom, such as solutions, emulsions, suspensions, powders, dusts, pastes or granules, are used in a known manner, for example by the preemergence method or postemergence method, as dressings or by mixing into the water supplied to cut flowers.

Examples of formulations are:

I. 20 parts by weight of the compounds of Example 5 are thoroughly mixed into 3 parts by weight of the sodium salt of diisobutylnaphthalenesulfonic acid, 17 parts by weight of the sodium salt of a ligninsulfonic acid obtained from sulfite waste liquor and 60 parts by weight of silica gel powder, and the mixture is milled in a hammer mill. By finely distributing the mixture in 20,000 parts by weight of water, a spray liquor which contains 0.1% by weight of the active ingredient is obtained.

II. 3 parts by weight of the compound of Example 15 are thoroughly mixed with 97 parts by weight of finely divided kaolin. A dusting agent which contains 3% by weight of the active ingredient is obtained in this manner.

III. 30 parts by weight of the compound of Example 15 are thoroughly mixed with a mixture of 92 parts by weight of silica gel powder and 8 parts by weight of liquid paraffin, which was sprayed on to the surface of the silica gel. A formulation of the active ingredient having good adhesion is obtained in this manner.

IV. 40 parts by weight of the compound of Example 15 are thoroughly mixed with 10 parts of the sodium salt of a phenolsulfonic acid/urea/formaldehyde condensate, 2 parts of silica gel and 48 parts of water. A stable aqueous dispersion is obtained. By dilution with 100,000 parts by weight of water, an aqueous dispersion which contains 0.04% by weight of active ingredient is obtained.

V. 20 parts of the compound of Example 15 are thoroughly mixed with 2 parts of the calcium salt of dodecylbenzenesulfonic acid, 8 parts of a fatty alcohol polyglycol ether, 2 parts of the sodium salt of a phenolsulfonic acid/urea/formaldehyde condensate and 68 parts of a paraffinic mineral oil. A stable oily dispersion is obtained.

VI. 90 parts by weight of the compound of Example 29 are mixed with 10 parts by weight of N-methyl-alpha-pyrrolidone, and a solution which is suitable for use in the form of very small drops is obtained.

VII. 20 parts by weight of the compound of Example 15 are dissolved in a mixture which consists of 80 parts by weight of xylene, 10 parts by weight of the adduct of from 8 to 10 mol of ethylene oxide with 1 mol of N-monoethanololeamide, 5 parts by weight of the calcium salt of dodecylbenzenesulfonic acid and 5 parts by weight of the adduct of 40 mol of ethylene oxide with 1 mol of castor oil. By pouring the solution into 100,000 parts by weight of water and finely distributing it therein, an aqueous dispersion which contains 0.02% by weight of the active ingredient is obtained.

VIII. 20 parts by weight of the compound of Example 29 are dissolved in a mixture which consists of 40 parts by weight of cyclohexanone, 30 parts by weight of isobutanol, 20 parts by weight of the adduct of 7 mol of ethylene oxide with 1 mol of isooctylphenol and 10 parts by weight of the adduct of 40 mol of ethylene oxide with 1 mol of castor oil. By pouring the solution into 100,000 parts by weight of water and finely distributing it therein, an aqueous dispersion which contains 0.02% by weight of the active ingredient is obtained.

IX 20 parts by weight of the compound of Example 29 are dissolved in a mixture which consists of 25 parts by weight of cyclohexanol, 65 parts by weight of a mineral oil fraction boiling within a range from 210° to 280° C. and 10 parts by weight of the adduct of 40 mol of ethylene oxide with 1 mol of castor oil. By pouring the solution into 100,000 parts by weight of water and finely distributing it therein, an aqueous dispersion which contains 0.02% by weight of the active ingredient is obtained.

The novel agents may also be present in these application forms together with other active ingredients, for example herbicides, insecticides, other bioregulators, fungicides and bactericides, or may be mixed with fertilizers and applied with them. Mixing with other bioregulators also results in synergistic effects, ie. the activity of the combination product is greater than the sum of the activities of the individual components.

The present invention relates in particular to the use of oxime ether compounds I for lowering the endogenous ethylene level in plants.

Ethylene is one of the plant hormones and is involved in the regulation of a wide range of growth, development and metabolic processes. Aging processes, dropping of leaves, blossoms and fruit, blossom and root formation, shoot and root growth, germination processes, the development of lateral buds and the release of secondary substances from the plant are examples of processes which are influenced by ethylene formed naturally by plants or by the action of external ethylene (Biochemistryand Physiology of Plant Hormones, SpringerVerlag New York 1989, pages 228–254). However, the formation of ethylene in plants is determined not only-by development factors but very substantially also by various environmental influences, for example drought, heat, cold, accumulated water, mechanical injury, pest attack, chemicals, etc., which as a rule produce a specific reaction pattern in the plant, for example aging processes or dropping of blossoms or fruit, as a result of increased ethylene production (BioScience 34/4 (1984), 234–238). A large number of physiological processes in plants can thus be regulated by lowering the endogenous ethylene level. The possibilities of beneficial use of this effect in practice are correspondingly varied. Increased yield and quality as a result of reduced dropping of blossoms and fruit or due to a prolonged vegetation phase, improved shelf life of the fruit or other plant parts and improvement in the life of cut flowers are examples.

It is known that various compounds have a regulatory effect on the ethylene balance of plants. However, comprehensive practical use has not been possible to date. The obstacles were, for example, the expensive preparation and the human toxicity in the case of aminoethoxyvinylglycine and the phytotoxicity and the relatively unspecific action in the case of aminooxyacetic acid, while 2,5-norbornadiene has high volatility and an unpleasant intrinsic odor. Cobalt salts and the silver salts used to a certain extent for keeping some cut flower species fresh are regarded as hazardous to health and environmentally polluting. Summaries are given in Ann. Rev. Plant Physiol. 1984, pages 155–189 and Bio-Science 34/4 (1984), 234–238.

For oxime ethers of other types, it has been shown (Plant Physiol. 90 (1989), 291–295) that they bind to the binding points specific for naphthylphthalamic acid in plant membranes and thus adversely affect the transport of the plant hormone auxin. Compounds having this action principle are suitable for interfering with the geotropism of the roots of cress, which is dependent on auxin transport (Plant Physiol. 66 (1980), 1190–1195). As shown in Table A, it has been found this is not true for compounds of the formula I, and, despite structural similarities, they therefore must be assigned a different type of action.

Use Examples

The comparative substances used were the compounds A (aminooxyacetic acid), B ($(CH_3)_2C=NO-CH_2CO_2CH_2CO_2CH_3$, Example 1 of EP-A 243 834) and C (naphthylphthalamic acid).

1. The effect of active ingredients on the geotropism of the root in cress was tested as follows: inert blocks measuring $1 \times 1 \times 4.5$ cm were wrapped in filter paper. These substrates were placed in Petri dishes each containing 5 ml of 0.01 mM, 0.1 mM and 1 mM active ingredient solution. The active ingredients had each been dissolved in aqueous buffer solution (HEPEA*-NaOH, 10 mM, pH 8). 10 cress seeds were aligned on each filter paper along the substrate edge in such a way that their root pole pointed to the edge. After incubation for about 48 hours at 25° C. and in darkness in a humid chamber, the geotropic behavior of the roots was rated. The roots grew downward and at right angles to the side of the substrate when the geotropism was not disturbed, but in the direction of the root pole already established in the seed, roughly horizontally beyond the edge, when the geotropism was disturbed.

*10 mmol of N-2-hydroxyethylpiperazine-N'-2-ethanesulfonic acid (HEPEA), brought into pH 8 with 2 N NaOH solution.

TABLE A

| Active ingredient | Root geotropism in cress |
|---|---|
| C | disturbed |
| Example 15 | not disturbed |
| Example 29 | not disturbed |

2. Inhibition of dry stress-induced ethylene in barley

In pots having a diameter of about 12.5 cm and a volume of about 500 ml, 80 barley seeds were placed on a peat culture substrate and cultivated under standardized conditions (21° C., 12 hour length of day, atmospheric humidity 70%) with an adequate supply of nutrients. After 7 days, the leaves of the young plants were sprayed with active ingredient solution (4 mg of active ingredient/pot). The active ingredients were dissolved in aqueous buffer solution (MEA**-NaOH, 50 mM, pH 6.1). A wetting agent (1-octylphenyl hexaglycol ether) was also added to the spray solution. Three days after treatment, the plants were cut, and 5 pieces were weighed and were incubated in an open drying oven at 30° C. until a weight loss of 10% resulted. In untreated plants, this dry stress leads to a considerable increase in ethylene biosynthesis (Plant Physiol. 68 (1981), 594–596). The stressed plants were transferred to glass cylinders which were sealed gas-tight with rubber septa. After incubation for about 4 hours in the dark, 1 ml of air was removed from each of the glass cylinders with the aid of a glass-tight syringe and the ethylene content was determined by gas chromatography.

**50 mmol of 2-(N-morpholino)-ethanesulfonic acid (MEA), brought into pH 6.1 with 2 N NaOH solution.

TABLE B

| Active ingredient | % inhibition compared with control | Toleration by plants* |
|---|---|---|
| A | 61% | — |
| B | 21% | + |
| Example 15 | 44% | + |
| Example 29 | 53% | + |

*The rating was carried out three days after treatment;
+ denotes good toleration and − denotes poor toleration.

3. Inhibition of ethylene formation in rape leaf disks

Disks were punched out from leaves of rape plants about 4 weeks old and were preincubated for about 16 hours with 1 ml of active ingredient solution containing 20 μg of active ingredient, then transferred to a tube and sealed gas-tight with a rubber septum. After about 4 hours, the amount of ethylene formed was determined by gas chromatography. The active ingredients were dissolved in aqueous buffer solution (MEA-NaOH, 50 mM, pH 6.1).

TABLE C

| Active ingredient | % inhibition compared with control |
|---|---|
| A | 79% |
| B | 62% |
| Example 15 | 64% |
| Example 29 | 71% |

4. Inhibition of ethylene formation in sunflower cell suspensions

Cell suspension cultures of the sunflower biosynthesize the phytohormone ethylene by a route identical to that of the plant (Table D). They are therefore suitable as a test system for finding novel inhibitors of ethylene biosynthesis (Plant Physiology 87 (1988), 510–513).

TABLE D

| Agent containing active ingredient No. | Concentration (M) | Inhibition of ethylene formation 4 days after treatment (%, based on control) |
|---|---|---|
| Untreated | — | 0 |
| Example 15 | $10^{-5}$ | 79 |
| B | $10^{-5}$ | 60 |

The novel agent leads to a greater inhibition of ethylene formation than the comparative agent.

5. Inhibition of the wilting of blossoms in cut flowers (carnations).

Freshly cut commercially grown carnations were placed in 80 ml of active ingredient solution containing 0.625 μmol of active ingredient/ml (unless stated otherwise). Water consumed by the carnations was replenished daily. The active ingredients were dissolved in aqueous buffer solution (HEPEA-NaOH, 10 mM, pH 7.5). The bactericide chloramphenicol (50 μg/ml) was also added to the active ingredient solution. Table E shows the percentage of wilted carnations on the day when all blossoms of the control were found to have wilted.

TABLE E

| Active ingredient | % of wilted carnations after 12 days |
|---|---|
| Control | 100% |
| Ag+ (0.125 μmol/ml) | 0% |
| A | 0% |
| B | 0% |
| Example 15 | 0% |

We claim:

1. A method for lowering the endogenous ethylene level in plants, which comprises applying to the plants or their habitats an ethylene-reducing effective amount of an oxime ether derivative of the formula I $$R^1R^2C{=}NO{-}CH_2{-}COOR^3 \qquad \text{I}$$

where $R^1$ and $R^2$ independently of one another are each hydrogen or $C_1$-$C_6$-alkyl or, together with the carbon atom to which they are bonded, are $C_5$- or $C_6$-cycloalkyl and $R^3$ is hydrogen or $C_1$-$C_6$-alkyl.

2. The method of claim 1, wherein $R^1$ and $R^2$, together with the carbon atom to which they are bonded, are cyclohexyl and $R^3$ is hydrogen or methyl.

3. The method of claim 1, wherein $R^3$ is hydrogen.

4. The method of claim 1, wherein $R^1$ and $R^3$ are each methyl or, together with the carbon atom to which they are bonded, are cyclohexyl and $R^3$ is hydrogen.

* * * * *